(12) United States Patent
Heigl

(10) Patent No.: US 8,295,911 B2
(45) Date of Patent: Oct. 23, 2012

(54) MOTION CORRECTION FOR TOMOGRAPHIC MEDICAL IMAGE DATA OF A PATIENT

(75) Inventor: Benno Heigl, Coburg (DE)

(73) Assignee: Siemens Aktiengesellschaft, München (DE)

(*) Notice: Subject to any disclaimer, the term of this patent is extended or adjusted under 35 U.S.C. 154(b) by 918 days.

(21) Appl. No.: 12/316,381

(22) Filed: Dec. 11, 2008

(65) Prior Publication Data
US 2009/0149741 A1 Jun. 11, 2009

(30) Foreign Application Priority Data
Dec. 11, 2007 (DE) .......... 10 2007 059 602

(51) Int. Cl.
A61B 8/00 (2006.01)
G06K 9/00 (2006.01)
(52) U.S. Cl. .......... 600/424; 382/107; 382/131
(58) Field of Classification Search .......... None
See application file for complete search history.

(56) References Cited

U.S. PATENT DOCUMENTS

| | | | | |
|---|---|---|---|---|
| 4,144,569 A | * | 3/1979 | Wagner | 378/11 |
| 4,712,560 A | * | 12/1987 | Schaefer et al. | 600/413 |
| 4,730,620 A | * | 3/1988 | Bailes | 600/410 |
| 4,779,620 A | * | 10/1988 | Zimmermann et al. | 600/410 |
| 4,858,128 A | * | 8/1989 | Nowak | 382/131 |
| 4,994,965 A | * | 2/1991 | Crawford et al. | 378/95 |
| 5,251,128 A | * | 10/1993 | Crawford | 600/425 |
| 5,287,276 A | * | 2/1994 | Crawford et al. | 378/4 |
| 5,552,605 A | * | 9/1996 | Arata | 250/363.04 |
| 6,233,476 B1 | * | 5/2001 | Strommer et al. | 600/424 |
| 6,259,942 B1 | * | 7/2001 | Westermann et al. | 600/426 |
| 6,879,656 B2 | * | 4/2005 | Cesmeli et al. | 378/4 |
| 7,142,703 B2 | * | 11/2006 | Kaufman et al. | 382/131 |
| 7,599,540 B2 | * | 10/2009 | Koehler | 382/130 |
| 7,702,063 B2 | * | 4/2010 | Koehler et al. | 378/4 |
| 8,027,715 B2 | * | 9/2011 | Sayeh | 600/426 |
| 8,184,883 B2 | * | 5/2012 | Grass et al. | 382/131 |
| 2006/0074299 A1 | * | 4/2006 | Sayeh | 600/426 |
| 2006/0074304 A1 | * | 4/2006 | Sayeh | 600/427 |
| 2008/0221435 A1 | | 9/2008 | Rasche | |

FOREIGN PATENT DOCUMENTS
WO 2007017771 A2 2/2007
* cited by examiner

Primary Examiner — Tse Chen
Assistant Examiner — Angela M Hoffa

(57) ABSTRACT

A method and apparatus for motion correction of medical image data of a patient are provided. Medical image data is obtained in a tomographic image recording process by back-projection from a number of projection images. The position of a magnetic location sensor, which is arranged on a medical implant inserted into a patient is also determined as a function of time while the projection images are being recorded, by means of an electromagnetic location system and the position is taken into account in the back-projection of the projection images for motion correction purposes.

12 Claims, 1 Drawing Sheet

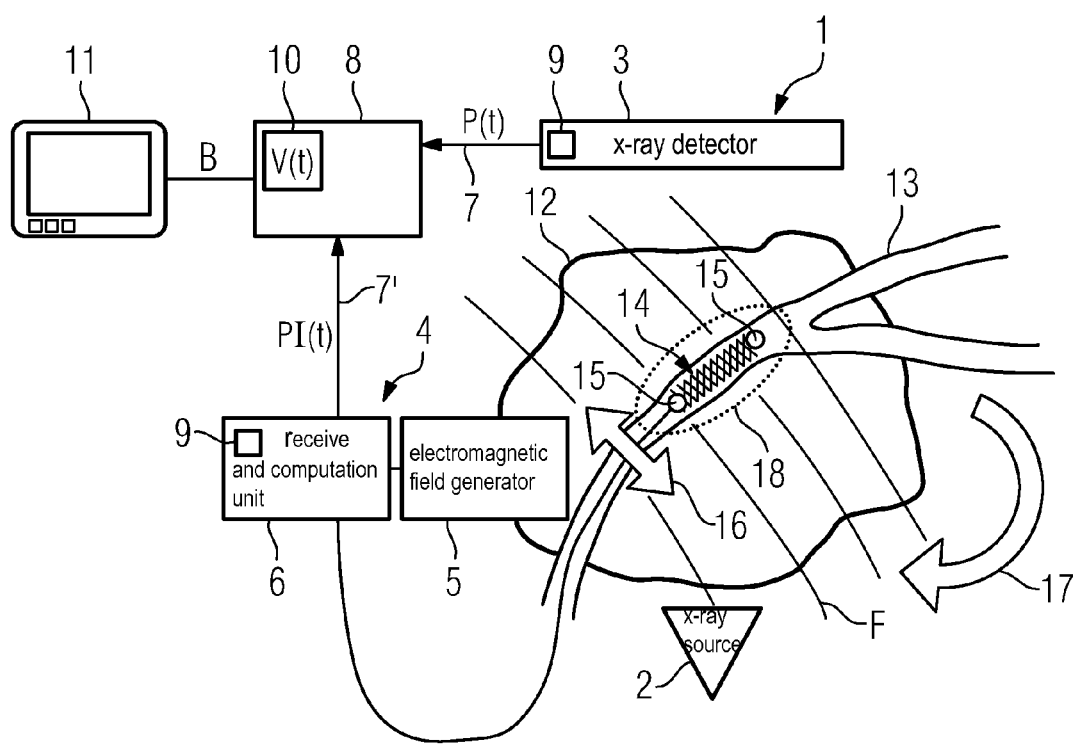

MOTION CORRECTION FOR TOMOGRAPHIC MEDICAL IMAGE DATA OF A PATIENT

CROSS REFERENCE TO RELATED APPLICATIONS

This application claims priority of German application No. 10 2007 059 602.4 DE filed Dec. 11, 2007, which is incorporated by reference herein in its entirety.

FIELD OF INVENTION

The invention relates to a method for motion correction for tomographic medical image data of a patient as well as to an apparatus for capturing medical image data using the method.

BACKGROUND OF INVENTION

A tomographic method (layer image recording method) is generally used to record in particular three-dimensional medical image data using an imaging system. The imaging system is for example a computed tomograph (CT), an x-ray C-arm, in particular an angiograph or a Single Photon Emission Computed Tomograph (SPECT). The medical image data is obtained by measuring projection images of a body region of a patient in temporal succession one after another from different viewing angles. To measure these projection images, the medical imaging system has a measuring arrangement. In the case of a computed tomograph for example this measuring arrangement comprises an x-ray source and an x-ray detector, which are supported in a movable manner in a gantry.

The actual medical image data is calculated from the projection images during the course of a so-called back-projection. Since the projection images are captured over a specific time period, motion of the examined body region is necessarily registered as well. While voluntary patient motion can be largely avoided by securing the patient or by administering an anesthetic, this is not possible for motion stimulated by the vegetative nervous system. This relates for example to motion of the measured body region, associated with breathing, the heartbeat or peristaltic motion of an intestine.

When calculating the image data from the projection images, so-called motion artifacts result, which to some degree significantly impair the clinical benefit of the calculated data. If for example a stent is to be inserted into a coronary vessel of the heart of a patient, when the heart is measured using CT, motion causes blurring of the imaged coronary vessel, which makes it difficult to select an appropriate stent for the intervention.

To improve the quality of the image data several methods have been developed, of which an overview can be found in U.S. Pat. No. 6,708,052 B1. It is thus possible to capture the projection data in very rapid succession. Reducing the so-called acquisition time when measuring the projection data also reduces the occurrence of motion artifacts. However the shortening of the acquisition time is subject to technical limits, in particular if larger body regions are to be measured at once. Also the simultaneous use of a number of imaging systems of the same type, each capturing a part of the body region to be examined, can only be of limited assistance here.

So-called ECG gating provides a different route, measuring the ECG of the heart while the projection images are being captured. Then only the projection images corresponding to a specific heart phase are used to calculate the image information. A further approach is to implement so-called ECG triggering, with which projection images are only measured when the heart is in a specific heart phase. ECG gating and ECG triggering have the disadvantage that they only correct heart motion. Gating also takes into account a patient's breathing.

The specialist article by M. Prümmer et al, "Cardiac C-arm CT: Efficient motion correction for 4D-FBP, 2006 IEEE Nuclear Science Symposium Conference Record", p. 2620 ff. describes a computational method for motion correction. Projection images of a body region to be examined, determined as a function of time using CT, are captured first. A sequence of medical image data is then calculated from the projection images. The so-called FDK method is used in combination with ECG gating here. The time-based medical image data thus determined, also referred to as 4D data in the specialist literature, contains information about the time-based deformation of the measured body region. The approach adopted by M. Prümmer et al in their work is that of calculating a displacement vector field from the time-based image data, said displacement vector field containing the change in all volume elements or voxels of the captured body region at any time. This displacement vector field is used to correct the originally measured projection images in respect of their location information. This corrected projection data then undergoes a further back-projection. The result is three-dimensional medical image data, in which the motion of the body region in question is corrected. This allows motion artifacts to be largely avoided in the three-dimensional medical image data. However this method is computationally very complex, requiring a high level of computation power.

U.S. Pat. No. 5,287,276 A discloses a motion correction method for computed tomography image data, in which, while the projection images are being recorded, ultrasound is used to detect the chest motion of the patient due to breathing and the detected motion is taken into account in the back-projection of the projection images.

SUMMARY OF INVENTION

The object underlying the invention is to specify a motion correction method for tomographic medical image data, which can be implemented simply and with reasonable outlay and which can be applied to any body region.

According to the invention this object is achieved by the feature combination in the independent claims. To implement the method a magnetic location sensor of an electromagnetic location system is used, being arranged on an implant inserted into the patient. While the projection images are being recorded, an electromagnetic location system is used to determine the position of the magnetic location sensor as a function of time. The position of the magnetic location sensor is taken into account in the back-projection of the projection images for motion correction purposes.

An electromagnetic location system with at least one magnetic location sensor is known per se for example from U.S. Pat. No. 6,233,476 B1. Here measured image information is combined with measured position information. It is thus possible for example to record medical image information before a medical intervention and to identify the position in the body of a medical implant already inserted into the body of a patient, to which a magnetic location sensor is assigned. This medical implant is a stent for example. When the medical implant is moved to its intended location, its position can be monitored continuously based on the constantly measured position information of the magnetic location sensor. The motion of the medical implant in the body of the patient can be monitored continuously, in particular on a display element, such as a monitor, by combining the initially measured image information with the position of the magnetic location sensor.

It is now recognized that an electromagnetic location system is not simply used to detect the position of a medical implant, which is provided with such a magnetic location sensor, as a function of time. Rather the location sensor is also exposed to the motion of the body region. It therefore moves necessarily with the body. The magnetic location sensor can therefore be used to detect the motion of this body region and to capture it as a function of time in the form of position information. The position information is now used to correct the projection images. Then during back-projection of the projection images the position of the magnetic location sensor is included in the back-projection calculation. Alternatively the projection images can also be corrected based on the position of the magnetic location sensor, in particular based on the change in the position of the location sensor compared with a predefined reference position. Finally the back-projection is carried out with the corrected projection images. The occurrence of motion artifacts is now completely or at least largely avoided. It is therefore possible for a diagnosing physician to evaluate the image data with a low error rate.

In one advantageous development a displacement vector field of an examination region of the patient is determined from the change in position of the location sensor. The position information of the magnetic location sensor, captured as a function of time, corresponds to this displacement vector field, if it is approximately assumed that the surrounding body region moves in the same manner as the location sensor. In other words the displacement vector field results in a simple manner from the measurement of the position of the location sensor by means of a simple vector-algebraic calculation.

The system time of the medical imaging system supplying the image data and the system time of the electromagnetic location system are expediently synchronized. To this end a system timer is assigned respectively to the medical imaging system and to the magnetic location system. Synchronizing the system times of the two system timers means that both system timers have the same system time after the synchronization process. This synchronization process is advantageously carried out at the start of every measurement using the medical imaging system and the magnetic location system. Measuring is carried out in particular in such a manner that measurements are taken with an identical measuring cycle with both measuring systems. In other words both the projection images of the medical imaging system and the position information of the magnetic location system have identical time stamps. Thus for every time stamp there is position information, from which the associated displacement vector field for this time can be calculated. This displacement vector field is then used to correct the projection image similarly measured at this time. This gives a 1:1 assignment between a projection image and a displacement vector field, so that only one projection image has to be corrected with one displacement vector field respectively.

In one advantageous development the displacement vector field is calculated for a time between two measurements of the magnetic location system by temporal interpolation from the two displacement vector fields of the two measurements. This means that deviations which may possibly occur due to the system can be corrected in the measuring cycle of the medical imaging system and of the magnetic location system such that a simultaneous displacement vector field is again present for every projection image, in order to correct the projection image.

In an expedient development the positions of at least two magnetic location sensors are captured. A mean displacement vector field is also calculated by means of an interpolation in a region around the location sensors. Such an interpolation is described for example in the specialist manual by M. J. D. Powell, "Radial basic functions for multivariable interpolation: a review", Clarendon Press, New York, 1987, ISBN 0-19-853612-7.

A number of location sensors are advantageously distributed over the body region of the patient to be examined. This allows spatial interpolation using the respectively measured change in position of the individual location sensors when calculating the displacement vector field. It is therefore also possible to capture non-uniform motion of the measured body region.

The at least one magnetic location sensor can be used to capture the position of the medical implant in the body of the patient at any time. The medical image data corrected using position information can be used to examine in particular the immediate area around the medical implant without motion artifacts. The implant can then be inserted without the possibility of motion artifacts resulting in an incorrect assessment of the insertion situation. Structurally small multi-axis coils in particular are used as the magnetic location sensors, as known per se for example from U.S. Pat. No. 6,233,476 B1. A number of these location sensors can also be assigned to a spatially extended medical implant.

In one advantageous variant a stent is used as the medical implant. The at least one magnetic location sensor assigned to the stent is used to monitor the insertion of said stent. A blood vessel, having a constriction into which the stent is to be inserted, is imaged sharply and without motion artifacts. It is therefore possible to locate the constriction precisely and to position the stent so that it bridges the constriction reliably after it has been dilated. This reduces in particular the risk that an incorrectly inserted stent will subsequently have to be removed by operation.

According to the method differently configured location sensors, for example location sensors configured as probes and/or location sensors that can be affixed to the body surface, can be used in addition to and in combination with location sensor arranged on implants. A mean displacement vector field is then calculated in a region around all the location sensors. This allows particularly efficient motion correction to be achieved.

The object is also achieved by an apparatus for capturing three-dimensional medical image data, comprising a medical imaging system, an electromagnetic location system with at least one magnetic location sensor and a correction unit, which is set up to correct the image data based on a measured position of the location sensor. The location sensor here is arranged on an implant, which is inserted or can be inserted into the body of a patient. The variants of the invention described in relation to the method and its advantages are to be applied appropriately to the apparatus.

BRIEF DESCRIPTION OF THE DRAWINGS

An exemplary embodiment of the invention is described in more detail below with reference to a drawing, in which the single FIGURE shows an apparatus for capturing three-dimensional medical image data.

DETAILED DESCRIPTION OF INVENTION

The illustrated apparatus comprises a medical imaging system 1 in the form of an x-ray C-arm. This system 1 has an x-ray source 2 and an x-ray detector 3. An electromagnetic location system 4 is also provided, having an electromagnetic field generator 5 and a receive and computation unit 6 for position determination. The x-ray detector 3 and the computation unit 6 are connected by way of communication interfaces 7,7' configured as data cables to a reconstruction computer 8. The x-ray detector 3 and the receive and computation unit 6 each have a system timer 9.

A correction unit 10 is assigned to the reconstruction computer 8, being configured as a computation module in particular in the form of software. A display element 11 is also assigned to the reconstruction computer 8.

The medical imaging system 1 is used to capture a body region of a patient as an examination region 12, only shown in outline in the FIGURE. It can be for example the heart, intestine or lung of the patient. A blood vessel 13 passes through the body region 12, likewise only shown in outline. A medical implant 14 configured as a stent is to be inserted into a constriction (not shown) in the blood vessel 13, with a magnetic location sensor 15 assigned respectively to both of its ends. During the course of the time-based measuring operation the body region 12 moves non-uniformly in the motion direction 16.

The stent 14 with its two magnetic location sensors 15 is inserted into the body region 12 during the course of measuring. It now has to be positioned precisely based on the image data to be measured and has to be dilated by means of a balloon catheter (not shown in the FIGURE).

Before the start of measuring the reconstruction computer 8 synchronizes the two system timers 9 of the imaging system 1 and the magnetic location system 4 by way of the two communication interfaces 7. Thus at the start of measuring the imaging system 1 and the magnetic location system 4 have an identical system time. During measuring the x-ray source 2 and x-ray detector 3 move in a synchronized manner in the rotation direction 17 in a gantry (not shown in the FIGURE). The projection images P(t) captured by the x-ray detector 3 as a function of time are transmitted by way of the communication interface 7 to the reconstruction computer 8.

While the projection images P(t) are being recorded, the electromagnetic field generator 5 of the electromagnetic location system 4 generates an electromagnetic field F. Position information PI(t) is determined as a function of time in the receive and computation unit 6 by means of the two location sensors 15. This position information PI(t) is transmitted by way of the communication interface 7' to the reconstruction computer 8. The measuring cycles of the imaging system 1 and of the magnetic location—system 4 are expediently identical here, so that position information PI(t) corresponds to each projection image P(t).

The projection images P(t) and position information PI(t) measured as a function of time are combined in the reconstruction computer 8. The correction unit 10 uses the position information PI(t) measured as a function of time to calculate a time-based displacement vector field V(t). The displacement vector field V(t) captures the motion of the two magnetic location sensors 15 attached to the stent 14 in the motion direction 16. It is taken into account here that the body region 12 may possibly be moving non-uniformly in the motion direction 16. To this end a mean displacement vector field is calculated by interpolation for a region 18 around the location sensors 15, said mean displacement vector field being contained in the displacement vector field V(t). The displacement vector field V(t) indicates the relative displacement of the body region 12 around the two location sensors 15 in relation to a predefined zero position of the two magnetic location sensors 15, which for example corresponds to their position at the start of measuring. The displacement vector field V(t) is then offset using the projection images P(t) in the correction unit 10, to eliminate the influence of the motion of the body region 12 on the projection images P(t) by computation.

The displacement vector field V(t) is included in the calculation of the back-projection of the projection images P(t) for the purposes of motion correction. The three-dimensional medical image data B thus calculated is displayed on the display element 11. This image data B has no or almost no evaluation artifacts due to the motion of the body region 12 in the motion direction 16.

A segment of the blood vessel 13 can thus be displayed sharply in the region 18 around the location sensors 15. The edges of the blood vessel 13 in particular are displayed sharply, so that the constriction, into which the stent 14 is to be inserted, can be identified precisely. Optionally three-dimensional medical image data B is measured repeatedly to control the insertion of the stent 14, in order to ensure the optimum insertion position of the stent 14.

The invention claimed is:

1. A method for motion correction for medical image data of a patient, comprising:
    determining a position of a magnetic location sensor by an electromagnetic location system as a function of time while a plurality of projection images are recorded in a tomographic image recording process by back projection, the magnetic location sensor arranged on a medical implant inserted into a patient;
    providing a motion correction of the projection images using the determined position; and
    back projecting the corrected images,
    wherein the medical implant is a stent.

2. The method as claimed in claim 1, further comprising determining a displacement vector field of an examination region of the patient for providing the motion correction of the projection images, the displacement vector field determined from a change in position of the location sensor.

3. The method as claimed in claim 2, further comprising synchronizing a system time of an imaging system recording the projection images with a system time of the electromagnetic location system.

4. The method as claimed in claim 2, wherein the displacement vector field is calculated for a time between two measurements of the electromagnetic location system by interpolation from the two displacement vector fields of the two measurements.

5. The method as claimed in claim 2, further comprising:
    wherein positions of a plurality of magnetic location sensors arranged on the implant are captured,
    calculating a mean displacement vector field via an interpolation in a region around the plurality of magnetic location sensors.

6. The method as claimed in claim 1, further comprising synchronizing a system time of an imaging system recording the projection images with a system time of the electromagnetic location system.

7. An apparatus for capturing medical image data, comprising:
    an imaging system configured to record a plurality of projection images;
    a reconstruction computer configured to obtain the medical image data by back-projection from the projection images;
    an electromagnetic location system comprising a magnetic location sensor, the magnetic location sensor is arranged on an implant adapted to be inserted into a patient, the location system configured to determine the position of the magnetic location sensor as a function of time while the projection images are being recorded; and a correction unit configured to correct the projection images based on the measured position, wherein the medical implant is a stent.

8. The apparatus as claimed in claim 7, wherein the correction unit is set up to determine a displacement vector field of an examination region of the patient from the position of the location sensor.

9. The apparatus as claimed in claim 8,
wherein a system timer is assigned respectively to the medical diagnosis device and the magnetic location system, and
wherein the correction unit synchronizes the two system timers at the start of measuring.

10. The apparatus as claimed in claim 8, wherein the correction unit calculates the displacement vector field for a time between two measurements by interpolation from the two displacement vector fields of the two measurements.

11. The apparatus as claimed in claim 8, wherein with the correction unit captures positions of a plurality of magnetic location sensors arranged on the implant and calculates a mean displacement vector field via an interpolation in a region around the location sensors.

12. The apparatus as claimed in claim 7,
wherein a system timer is assigned respectively to the medical diagnosis device and the magnetic location system, and
wherein the correction unit synchronizes the two system timers at the start of measuring.

* * * * *